(12) United States Patent
Cuypers et al.

(10) Patent No.: US 10,864,099 B2
(45) Date of Patent: Dec. 15, 2020

(54) IMMOBILISATION ELEMENT AND ADDITIVE MANUFACTURING METHOD FOR MAKING SAME

(71) Applicant: Orfit Industries N.V., Wijnegem (BE)

(72) Inventors: Steven Cuypers, Wijnegem (BE); Bogdan Bogdanov, Wijnegem (BE); Simon De Gruytere, Wijnegem (BE)

(73) Assignee: ORFIT INDUSTRIES N.V., Wijnegem (BE)

( * ) Notice: Subject to any disclaimer, the term of this patent is extended or adjusted under 35 U.S.C. 154(b) by 431 days.

(21) Appl. No.: 15/540,515

(22) PCT Filed: Dec. 23, 2015

(86) PCT No.: PCT/IB2015/059935
§ 371 (c)(1),
(2) Date: Jun. 28, 2017

(87) PCT Pub. No.: WO2016/108154
PCT Pub. Date: Jul. 7, 2016

(65) Prior Publication Data
US 2018/0001547 A1   Jan. 4, 2018

(30) Foreign Application Priority Data
Dec. 31, 2014   (BE) .................................. 2014/0853

(51) Int. Cl.
*B29C 64/118*   (2017.01)
*A61F 5/01*   (2006.01)
(Continued)

(52) U.S. Cl.
CPC ........ *A61F 5/0118* (2013.01); *A61F 5/05875* (2013.01); *A61F 5/37* (2013.01);
(Continued)

(58) Field of Classification Search
CPC .... A61F 5/3776; A61F 5/3715; A61F 5/3723; A61F 5/055; A61G 13/121; A61G 13/12;
(Continued)

(56) References Cited

U.S. PATENT DOCUMENTS

| 4,575,330 | A | 3/1986 | Hull |
| 2002/0136848 | A1* | 9/2002 | Yoshii .................. C08J 3/28 |
| | | | 428/35.7 |

(Continued)

FOREIGN PATENT DOCUMENTS

| CN | 1294021 A | 5/2001 |
| CN | 104203167 A | 12/2014 |

(Continued)

OTHER PUBLICATIONS

Peterson et al., "3D-Printed mechanochromic materials", Applied Materials & Interfaces, 2015, vol. 7, pp. 577-583.

(Continued)

*Primary Examiner* — Ophelia A Hawthorne
(74) *Attorney, Agent, or Firm* — Foley & Lardner LLP; Sunit Talapatra

(57) ABSTRACT

This invention relates to a method for manufacturing an individualized immobilization element for the non-invasive immobilization and/or mobilization of at least a segment of a body part of a patient in a predetermined position relative to a reference and/or in a pre-certain configuration. The method comprises the steps of (i) providing a data set that comprises a three-dimensional image of an outer contour of at least a part of the segment of the body part to be immobilized and/or mobilized and (ii) the manufacture of at least a part of the immobilization element by rapid manufacturing of a shape on the basis of said data set using a polymeric material containing a thermoplastic polymer having a melting point less than or equal to 100° C., wherein the (Continued)

polymer material contains a nucleating agent for enhancing the of the crystallization of the thermoplastic polymer.

21 Claims, 4 Drawing Sheets

(51) Int. Cl.

| | | |
|---|---|---|
| A61F 5/058 | (2006.01) | |
| B33Y 10/00 | (2015.01) | |
| B33Y 70/00 | (2020.01) | |
| B33Y 80/00 | (2015.01) | |
| B29C 64/153 | (2017.01) | |
| B29C 64/209 | (2017.01) | |
| A61F 5/37 | (2006.01) | |
| A61L 15/12 | (2006.01) | |
| G05B 19/4099 | (2006.01) | |
| B29L 31/00 | (2006.01) | |
| B29K 67/00 | (2006.01) | |
| B29K 101/10 | (2006.01) | |
| B29K 105/00 | (2006.01) | |
| B29K 105/16 | (2006.01) | |
| B29K 507/04 | (2006.01) | |

(52) U.S. Cl.
CPC ............ *A61F 5/3707* (2013.01); *A61L 15/12* (2013.01); *B29C 64/118* (2017.08); *B29C 64/153* (2017.08); *B29C 64/209* (2017.08); *B33Y 10/00* (2014.12); *B33Y 70/00* (2014.12); *B33Y 80/00* (2014.12); *G05B 19/4099* (2013.01); *B29K 2067/04* (2013.01); *B29K 2101/10* (2013.01); *B29K 2105/0005* (2013.01); *B29K 2105/162* (2013.01); *B29K 2507/04* (2013.01); *B29K 2995/0041* (2013.01); *B29L 2031/753* (2013.01); *G05B 2219/35134* (2013.01); *G05B 2219/49007* (2013.01)

(58) Field of Classification Search
CPC ................ A61G 13/1235; A61G 7/072; A61G 13/1265; E05B 75/00; A61B 90/18
See application file for complete search history.

(56) References Cited

U.S. PATENT DOCUMENTS

| | | | |
|---|---|---|---|
| 2005/0222529 A1 | 10/2005 | Cuypers et al. | |
| 2009/0316965 A1* | 12/2009 | Mailling | A43D 1/025 |
| | | | 382/128 |
| 2013/0072839 A1* | 3/2013 | Cuypers | A61F 5/05841 |
| | | | 602/7 |
| 2014/0081190 A1 | 3/2014 | Summit et al. | |
| 2015/0000679 A1 | 1/2015 | Cuypers et al. | |
| 2015/0047652 A1* | 2/2015 | De Mooij | A61B 6/0428 |
| | | | 128/869 |

FOREIGN PATENT DOCUMENTS

| | | |
|---|---|---|
| EP | 0 401 883 A1 | 12/1990 |
| EP | 1 582 187 | 10/2005 |
| EP | 1 996 107 | 8/2007 |
| GB | 2 455 926 A | 7/2009 |
| JP | 62-035966 A | 2/1987 |
| JP | H03-199417 A | 8/1991 |
| JP | 2014-516257 A | 7/2014 |

OTHER PUBLICATIONS

In the making: "Social, 3D printed cast for broken bones", YouTube, Internet, Sep. 2014, XP054976026, retrieved from the Internet: URL: https://www.youtube.com/watch?v=trtU1NzUBTI [retrieved on Aug. 24, 2015].

"Material Safety Sheet", Perstorp UK Ltd., Jan. 22, 2013, XP002755654, retrieved from the Internet: URL: http://downloads.makerbot.com/filament/PCL MSDS.pdf [retrieved on Mar. 18, 2016].

Tomonews US: "3D printed cortex cast takes the itch out of healing broken bones", Aug. 2013, XP0549760247, retrieved from the Internet: URL:https://www.youtube.com/watch?v=6u_varjAUjQ [retrieved on Aug. 24, 2015].

International Search Report issued in International Patent Application No. PCT/IB2015/059935 dated Apr. 4, 2016.

\* cited by examiner

IMMOBILISATION ELEMENT AND ADDITIVE MANUFACTURING METHOD FOR MAKING SAME

CROSS-REFERENCE TO RELATED APPLICATIONS

This application is the National Phase of International Patent Application No. PCT/IB2015/059935, filed Dec. 23, 2015, published on Jul. 7, 2016 as WO 2016/108154 A1, which claims priority to Belgium Patent Application No. 2014/0853, filed Dec. 31, 2014. The contents of these applications are herein incorporated by reference in their entirety.

BACKGROUND OF THE INVENTION

The present invention relates to a method for manufacturing an individualized immobilization element for the non-invasive immobilization and/or mobilization of at least a segment of a body part of a patient at a predetermined position relative to a reference and/or in a predetermined configuration, as described in the preamble of the first claim. Immobilization and/or mobilization are usually carried out in such a way that account is taken of the patients' pathological picture.

External appliances for the immobilization and/or mobilization of a body part or part thereof as such are known, in recent years they have known considerable development. They are typically used in the rehabilitation of a.o. orthopedic, traumatic, surgical, geriatric, pediatric and neurological diseases. Orfit Industries offers such tools, which are typically intended to support or immobilize bony structures and/or soft tissue in a predetermined position and/or configuration.

Examples of external devices are customizable thermoplastic splint materials, which are made available in a limited number of standard sizes, or a limited number of sizes. Depending on the nature of the material in which they are made and depending on the intended purpose, the devices can be made in a material selected in such a way that their shape and dimensions may be adapted to the patient. Personalized splint materials, which may be formed immediately on the body part to be immobilized, for example the arm or leg or the torso, are also offered. Such splints are usually made by cutting a sheet of a thermoplastic material according to a certain size, heating the sheet to a temperature at which the material becomes deformable, positioning the sheet on the body part involved, shaping it immediately on the body part and then allowing it to cool. Finally, the splint is closed along the edges (see FIG. 1A) in order to effectuate the envisaged mobilization/immobilization. This is for example disclosed in EP0401883. Fixation can be accomplished using the means known to the skilled person, for example, interlocking, co-operating hook and loop straps or the like, or a zipper attached along the edges of the splint. Since the connecting means are usually made of a different material than the splint, application of the closure on the splint usually requires a separate production step and often requires an additional operation. However, the presence of such connecting means increases the risk of contamination with micro-organisms. Because the material of the connecting means typically has different mechanical properties than the material of which the splint is made, the degree to which the splint fits and is capable of immobilizing, may vary. Orthotics and prosthetics have evolved in a similar way as described above.

Immobilization elements know a wide application in radiation therapy and diagnostic imaging for which a wide range of equipment is available, inter alia, an accelerator, NMR, MRI, CT etc. Especially in this latter applications a correct positioning of the body part with respect to the radiation source is important, in order to ensure that the radiation is directed at the body part to be treated and the risk of irradiating surrounding healthy tissue is kept to a minimum. A reproducible positioning is of utmost importance in fractionated therapy, in which a segment, i.e. one or more portions of a body part are repeatedly subjected to irradiation, with intermittent time intervals between subsequent irradiation sessions. Stereotactic procedures also require a precise positioning and fixation of the relevant part of the body to permit localizing and targeting of the relevant part of the body part. The stability of the immobilization element plays an important role in the above-mentioned applications, by which is meant that the ability of the body part to be immobilized to be moved or displaced after having been immobilized, is limited to less than a few mm, preferably up to 0.5 mm or even less.

In radiation therapy and diagnostic imaging often use is made of a bench or table, to which the patient is positioned in a supine or prone position, while the segment of the body part to be treated is immobilized at the desired position in a desired configuration. In order to enable achieving the desired immobilization Orfit Industries has developed a variety of masks which are placed over a portion of the body, for example the head, a portion of the shoulders and a portion of the chest of the patient, and are connected to the bench or table. In order to guarantee an optimal fit with the body part to be immobilized, to ensure that the inner surface of the sheet of the thermoplastic material fits as close as possible to the outer contours of the body part to be immobilized, such as head, shoulders and/or chest, and the intended immobilization is achieved, the mask is formed directly on the patient's body. Fastening of the mask to the patient table is made possible by the presence of one or more connecting profiles along the edge of the mask which can be connected to a corresponding profile on the table. The connection profiles are usually made in a different material than the mask, and are attached to the mask using an adhesive, by welding or using a mechanical connection. An example of a mask provided with connecting profiles is shown in FIG. 1B.

In a frequently used method for manufacturing splints and masks, especially when using ε-polycaprolactone as the material for the mask, the material is formed directly on the body part. Shaping of the material may require some time, in particular cooling and hardening of the material may take 10 minutes or more. In the course of this period of time the patient is not allowed to move, reason for which removing of the thermoplastic material after a short period of time is not possible. This method is therefore perceived as particularly unpleasant, in particular by children or patients suffering from claustrophobia.

EP1582187 discloses a process for manufacturing an immobilization mask, wherein from a sheet of a thermoplastic material, in particular c-polycaprolactone, a part is cut which is sufficient for producing a mask. The sheet is then heated and positioned on the body part to be immobilized, for example, the face and the head. Shaping of the sheet into an individualized mask takes place by forming the sheet in such a way on the face and around the head that the inner surface of the sheet which contacts the head, follows the outer contours of the face and head. After having being shaped and cooled down, a personalized or individualized mask is obtained which is ready to be used. Personalized masks produced according to that method typically have a shape that more or less follows the contours of the face and head, as well as the contours of the details of the face, for example, the nose and/or mouth, and/or eyes. In order to achieve the desired fixation force, the edges of the mask are attached to the table on which the head rests, using connecting profiles (FIG. 1C). The direct shaping on the body makes it possible to achieve optimal immobilisation and to restrict the possibility of moving of the head within the mask to a maximum of 1 to 2 mm. The fixation force pulls the mask to the table or support on which the head is positioned.

EP1996107 discloses a process for producing an immobilization mask wherein the body part to be immobilized is subjected to a three-dimensional scan with the purpose of obtaining three-dimensional image data on the shape and dimensions of the body portion. Based on this scan, a replica of the body part to be immobilized is produced. The immobilization mask is then produced by shaping a sheet of a thermoplastic material to the replica. Because production of an immobilization mask on a replica may lead to a too tight fit on the patient, the raw image data are modified. The production of the mask and the initial scan of the patient for obtaining the set of 3D image data can be carried out at the same location, for example, in the institution where radiotherapy takes place, or at different locations. However, the manufacture of the replica is time-consuming and expensive.

BRIEF DESCRIPTION OF THE INVENTION

This invention aims at providing a method which allows for a further optimization of the method for manufacturing an individualized immobilization element, where the immobilization element may immediately be produced in the desired shape and dimensions, and moulding of a sheet of a thermoplastic material to the body part to be immobilized is no longer required.

The present invention further seeks to provide a method for the manufacturing of an individualized immobilization element, which, after having been manufactured is as such suitable for use with an intended patient, and where the immobilisation element if necessary, can be re-shaped by heating and shaping of the polymer material.

This invention in particular aims at providing a standardized method for manufacturing individualized means for immobilizing a body part or a segment thereof and means which may be individualized for such immobilization, wherein the immobilization means are suitable for use in applications such as radiation therapy, diagnostic imaging including NMR, MRI, CT, etc.

This invention in particular seeks to utilize in an efficient manner data that are related to the shape and dimensions of a body part to be immobilized for the production of means for immobilizing the body part, and are obtained using non-invasive imaging techniques such as computed tomography (CT), magnetic resonance imaging (MRI), 3-D optical imaging, ultrasound, or laser scanners (3DS) or any other imaging technology.

A further optimized method for manufacturing an individualized immobilization element in the desired shape and with the desired dimensions, is achieved according to the invention with a method showing the technical features of the characterizing part of the first claim.

To this end, the method of this invention is characterized in that it comprises the steps of (i) providing a data set that comprises a three-dimensional image of an outer contour of at least a portion of the segment of the body part to be immobilize and/or mobilized and (ii) manufacturing of at least a part of the immobilization element by rapid manufacturing of a shape based on said data set, using a polymeric material containing a thermoplastic polymer having a melting point less than or equal to 100° C., wherein the polymer material contains a nucleating agent capable of enhancing crystallization of the thermoplastic polymer, wherein at least a portion of an inner surface of the shape has an inner contour which is complementary to the outer contour of the segment of the body part to be immobilized and/or mobilized.

Additive manufacturing offers the advantage that an immobilization element may be immediately manufactured in the desired dimensions, the desired shape and any desired configuration, using the data set that comprises a three-dimensional image of an outer contour of the segment of the body part to be immobilized and/or mobilized. A thus produced immobilization element is often suitable for immediate use without requiring further adjustments or shaping.

If necessary, the immobilization element may however after having been manufactured, be subjected to further shaping in order to provide an optimum individualization or in order to adapt the immobilization element in the course of time for example to fit to the changing shape or dimensions of the to be immobilized segment of the body part. This further shaping is rendered possible because the polymeric material of which the immobilization element is made comprises a thermoplastic material. The use of a thermoplastic material also offers the possibility of producing a plurality of immobilization elements in standard sizes, and of adapting them afterwards by thermo-forming to the specific size and shape of the patient. By using a thermoplastic material with a melting point which is less than or equal to 100° C., this forming may be carried out directly on the body part to be immobilized or mobilized, so that an optimal fit can be guaranteed.

The use of additive manufacturing for the manufacturing of an individualized immobilization element not only permits improving comfort to the patient during the production of the immobilization element, but the immobilization and/or mobilization properties themselves may be improved as well. To produce the data set that includes the three-dimensional image of the outer contours of the segment of the body part to be immobilized, which dataset will provide the basis from which the immobilization element is to be manufactured, a temporary immobilization of the corresponding segment of the body part is sufficient. It is namely sufficient to reduce the risk to movements in the course of the image capturing only. This can be achieved in many different ways, for example using a net or restraining belts or any other means known to the skilled person. Such a temporary immobilization offers considerably more comfort than the method used when thermoforming a thermoplastic material, wherein the body part to be immobilized is covered with the sheet, after which the sheet is formed on the part of the body and left there until the sheet has sufficiently cooled. The shaping of a sheet of a thermoplastic material can be time consuming, since an optimal future immobilization requires that the shape of the mask follows the shape of the body part as close as possible, for example head and face, and the details of the shape for receiving the eyes, nose, mouth and ears, have to be formed manually by pulling and moulding the thermoplastic material thereon. Experience has shown that in the course of the production of the mask, the shaping process is seen by the patient as the most traumatic act, particularly in case a mask is produced which is intended for the immobilization of the head and/or face. The reason is that the face remains covered by the material for the mask for a considerably long period of time and a lot of pulling and fitting actions must be performed. Because of the hardness of the sheet in combination with the use of a closed sheet material, the thermoplastic material is experienced as unpleasant and tight, especially if the shaping takes longer and is somewhat more complex. This problem is also encountered when immobilization elements are produced which must be applied on soft tissues, such as breast tissue.

Furthermore, the production of an immobilization element based on a data set opens the possibility of performing a reproducible modification of the data set where necessary or desirable, according to predefined criteria, in order to allow an optimal positioning and an optimal fit.

The present invention offers a solution to the aforementioned problems and makes it possible to provide a personalized immobilization element, thereby avoiding direct contact of the skin with the hot polymer sheet in the course of the shaping process, or at least to reduce that contact to a minimum.

The use of an immobilization element which has been manufactured by means of additive manufacturing further provides the advantage that a smaller fixation force or immobilization force suffices to achieve the desired positioning, immobilization and stability of the immobilization element. Also, the occurrence of undesirable pressure points due to pressure applied by the element to the skin and/or weak parts, can be kept to a minimum. The use of a three-dimensional image of the segment of the body part to be immobilized for the manufacturing of the shape namely allows applying more small scale details of the body segment to the immobilization element. Thus, it is for example possible to apply much more details of the shape of the nose, eyes and/or ears to the mask and to better follow the dimensions, which is much more difficult with the thermoforming of a sheet of a thermoplastic material as known from the state of the art which, when being shaped rather follows or adapts the general, crude contours. The presence of small scale shape details provides a plurality of positioning points which allow achieving an accurate local positioning of the immobilization element on the body segment to be immobilized, and which at the same time limit the possibility to move, even when using small fixation forces. This in contrast to the prior art, where the fixation force significantly contributes to achieving the desired immobilization. With fixation force is meant the force exerted by the immobilization element to the segment of the body part to be immobilized, during use.

Additive manufacturing as a technique for manufacturing an immobilization element further offers the advantage that at each position on the immobilisation element, a selected material thickness may be installed, taking into account the properties, in particular mechanical properties and fixation strength required or recommended at a given position. An important advantage is that the immobilization element may have a constant material thickness over the entire immobilization element so that the radiation transparency is the same over the entire immobilization element. However, if so desired, it is also possible to locally vary the thickness of the material, for example, to locally alter the radiation transparency, or to locally modify the mechanical properties. This is an important advantage in comparison with the known technique of thermoforming as described above, where the possibilities for controlling the thickness of the material are very limited and where the material located on the face located at the position of eyes, nose and mouth, usually has a different thickness as a result of stretching of the material in the vicinity of the connecting profile with which the mask is attached to the patient table.

The use of additive manufacturing for the manufacture of an immobilization element offers the additional advantage that material waste can be significantly reduced, as only the amount of material is used which is necessary for the production of the immobilization element. Unused material can be recycled. This in contrast to the known method wherein for example from a rectangular or square sheet of a thermoplastic material, a piece is cut which is sufficient for producing the immobilization element, and wherein the unused pieces of thermoplastic material are simply disposed as waste. Moreover, at positions which correspond to the position of the eyes, nose or nostrils, ears, etc. apertures may be provided already during the production of the immobilization element, thereby increasing the comfort of the patient and permitting material loss to be reduced to a minimum. Also, connecting means for attaching the immobilization element to a patient table can be simultaneously produced in one piece with the immobilization element into the desired shape and dimensions and at the desired position.

Within the scope of this invention immobilization and/or mobilization element is understood to mean a wide variety of devices capable of immobilizing and/or mobilizing a body part or a part thereof. Examples include a mask for the immobilization of a part of or the entire face or head, a mask for the immobilization of a part of or the entire chest, a splint for a part of or an entire arm or leg, or for the mobilization of an orthosis or a prosthesis holder for a body part, but other examples also are within the scope of this invention. Where in this patent application. "immobilization" is mentioned, both immobilization and mobilization are to be included.

The immobilization element obtained with the method of this invention can be used in a wide range of applications and is suitable for use with humans and animals, but also for the immobilization of articles.

The polymer material used in the method of this invention for the manufacture of the immobilization element using additive manufacturing, contains a nucleating agent for accelerating the crystallization rate of the thermoplastic polymer. This is of particular importance because of the relatively low melting temperature of the thermoplastic polymer, and especially if the use of a coolant is not intended. The nucleating agent may be present in the polymeric material or may be mixed with the thermoplastic polymer. In practice, the nucleating agent will usually be mixed with the thermoplastic polymer during the melting of the thermoplastic polymer in the additive manufacturing process.

The nucleating agents known to the skilled person and considered suitable by him can be used. Examples of nucleating agents suitable for use with this invention include particles of inorganic materials such as talc, calcium carbonate, pigments having a suitable particle size, or organic materials, for example polymers having a higher melting temperature than the thermoplastic material, terephthalic acid, but other nucleating agents may also be used. The amount of nucleating agent will be selected by the skilled person in such a way that a sufficiently fast crystallisation may be achieved, at a minimal risk to adversely affecting the mechanical properties and the transparency of the polymeric material for the relevant energy, so that the polymeric material continues to be suitable for the intended application. The amount of nucleating agent added may vary depending on the nature of the nucleating agent selected. The nucleating agent will usually be present in an amount ranging from 0.05 to 15.0 wt. % with respect to the amount of thermoplastic polymer, more preferably 0.5 to 10.0 wt. %, most preferably between 0.5 and 8 wt. %, in particular between 2.0 and 8.0 wt. % relative to the weight of the thermoplastic polymer.

Other nucleating agents suitable for enhancing the crystallization of the thermoplastic polymer include nanoparticles, in particular, organically modified clay and carbon nano-particles, in particular carbon nanotubes. Preferably, the thermoplastic polymer contains between 1.0 and 15.0 wt. % of an organic modified clay, preferably between 2.0 and 10.0 wt. %, more preferably between 3.0 and 8.0 wt. % relative to the weight of the thermoplastic material. In case carbon nanoparticles or carbon nanotubes are used, the thermoplastic polymer preferably contains between 0.01 and 10.0 wt. % of carbon nano-tubes, more preferably between 0.1 and 5.0 wt. %, relative to the weight of the thermoplastic polymer.

If it is the intention to dispense with the presence of a nucleating agent in the polymeric material, it may be decided to cool the polymeric material as soon as possible after the printing. This may for example be achieved by carrying out the additive manufacturing process in a refrigerated room, or by spraying a cooling gas, for example a liquid inert gas as $N_2$, Ar, He or cold $CO_2$ onto the printed polymer.

The presence of nanoparticles dispersed in the thermoplastic polymer, in particular the presence of exfoliated nanoparticles dispersed in the thermoplastic polymer, offers particular advantages both (luring the manufacturing process of the individualized immobilization element, as well as afterwards. The inventors have found that the shrinkage upon cooling of the polymeric material containing the thermoplastic polymer, can be significantly reduced. This significantly simplifies the process of production of the immobilization element in the desired or intended size. Because of the reduced shrinkage, there is much less the need to edit the data of the data set representative of the outer contours of the segment of the body part that needs to be immobilized to provide an offset, that should take this shrinkage into account and should make it possible for the immobilisation element to have a shape and dimensions which correspond as closely as possible to the shape and dimensions of the segment of the body part to be immobilized, and there is much less need to edit the data of the data set to provide an immobilization element which on the one hand leaves sufficient space to be sensed as somewhat comfortable, and on the other hand fits sufficiently tight to the segment of the body part to be immobilized and guarantees a sufficient stability.

The inventors have further found that the presence of nano-particles, in particular exfoliated nano-particles, increases the viscosity of the polymer in the molten state and is able to accelerate crystallization of the thermoplastic material. The accelerated crystallization permits to shorten the production time, which is important since in the process of additive manufacturing, the immobilization element is built up layerwise. For example, the small layer thickness of one or a few micrometre entails the necessity of depositing a large number of successive layers on top of each other, but the deposition and solidification and/or crystallization of the individual layers can be time consuming. The combination of the increased viscosity and accelerated crystallization permits to minimise the risk of spreading or flowing of the molten material (luring additive manufacturing, and to ensure that material deposition is carried out in accordance with a shape such as controlled by the data of the three-dimensional dataset. The combination of the increased viscosity and accelerated crystallization further permits to dispense with the use of a model or die to support the three-dimensionally shaped immobilization element in the course of the additive manufacturing. This use of a model or die would otherwise require a separate operation for producing the replica which should correspond as close as possible to the body part or segment thereof that is to be immobilized. This invention, however, does not exclude the use of such a replica or another mould and also includes additive manufacturing techniques in which use is made of supporting materials, such as the technique of selective laser sintering.

For the manufacturing of the immobilization and/or mobilization element of this invention, the polymeric material may contain a wide variety of thermoplastic polymers, such as those generally known to those skilled in the art. Suitable thermoplastic polymers include thermoplastic elastomers, thermoplastic polyurethane, thermoplastic polyisoprene, thermoplastic polyesters, thermoplastic polyolefins, polyvinyl chloride, polystyrene, or a blend of two or more of these polymers. More preferably, ε-polycaprolactone is used. In a further embodiment, the polymeric material may also contain an amount of one or more thermosetting materials.

This invention also relates to a method for manufacturing an individualized immobilization element for the non-invasive immobilization and/or mobilization of at least a segment of a body part of a patient, at a predetermined position relative to a reference and/or in a predetermined configuration, the method comprising the steps of (i) providing a data set that comprises a three-dimensional image of an outer contour of at least a portion of the segment of the body part to be immobilized and/or mobilized and (ii) manufacturing of at least a part of the immobilization element by rapid manufacturing of a shape based on said data set, using a polymeric material containing a thermoplastic polymer having a melting point below or equal to 100° C., wherein at least a portion of an inner surface of the shape has an inner contour which is complementary to the outer contour of the segment of the body part to be immobilized and/or mobilized, and wherein the polymer material is deposited in the molten or softened state, or is at least partially cross-linked after having been deposited, after which the polymer material is cooled.

Cooling of the material has the purpose of achieving hardening, solidification and/or at least a partial crystallization. Cross-linking of the material is preferably carried out while the material is still at least partly molten or softened, in other words, while the material is still in the molten or softened state.

The thermoplastic polymer containing the polymeric material is preferably used as a filament, in particular a multi- or monofilament. The use of a monofilament is preferred, particularly when use is made of fused deposition modelling (FDM) as additive manufacturing technique for the production of the immobilization element. In another embodiment the thermoplastic polymer-containing polymer material is used as a powder, in particular with the use of selective laser sintering (SLS) as additive manufacturing technique for the production of the immobilization element.

This invention also relates to a monofilament of a polymeric material, which contains a thermoplastic polymer having a melting point below or equal to 100° C., and a nucleating agent for enhancing the crystallization of the thermoplastic polymer. The polymeric material has a composition as described above and may contain exclusively consist of one or more thermoplastic polymers and a nucleating agent, or it may contain additional components as described above. This invention also relates to a monofilament made from a thermoplastic polymer or a mixture of two or more thermoplastic polymers having a melting point of below or equal to 100° C.

A particularly preferred embodiment of the invention relates to a method for manufacturing an individualized immobilization element for the non-invasive immobilization and/or mobilization of at least a segment of a body part of a patient at a predetermined position relative to a reference and/or in a predetermined configuration, the method comprising the steps of
  (i) providing a data set that comprises a three-dimensional image of an outer contour of at least a portion of the segment of the body part to be immobilized and/or mobilized and
  (ii) manufacturing of at least a part of the immobilization element by rapid manufacturing of a shape based on said data set, using a filament of a polymeric material, wherein the polymeric material contains a thermoplastic polymer having a melting point less than or equal to 100° C., wherein at least a portion of an inner surface of the shape has an inner contour which is complementary to the outer contour of the segment of the body part to be immobilized and/or mobilized and wherein the filament of the polymeric material is deposited in the molten or softened state, after which the polymeric material is cooled. In a preferred embodiment, the molten or softened material is at least partially cross-linked before being cooled.

In a preferred embodiment, the polymeric material from which the filament is produced contains a nucleating agent for enhancing the crystallization of the thermoplastic polymer, in particular nano-particles, more particularly nano-particles of an organically modified clay or carbon nanotubes, in particular, carbon nanotubes having a multi-layer wall.

This invention further relates to the use of a monofilament of a polymeric material, which contains a thermoplastic polymer having a melting point below or equal to 100° C. as described above for the manufacture of an immobilization element.

DETAILED DESCRIPTION OF THE INVENTION

THERMOPLASTIC POLYMERS

Figure 1A:
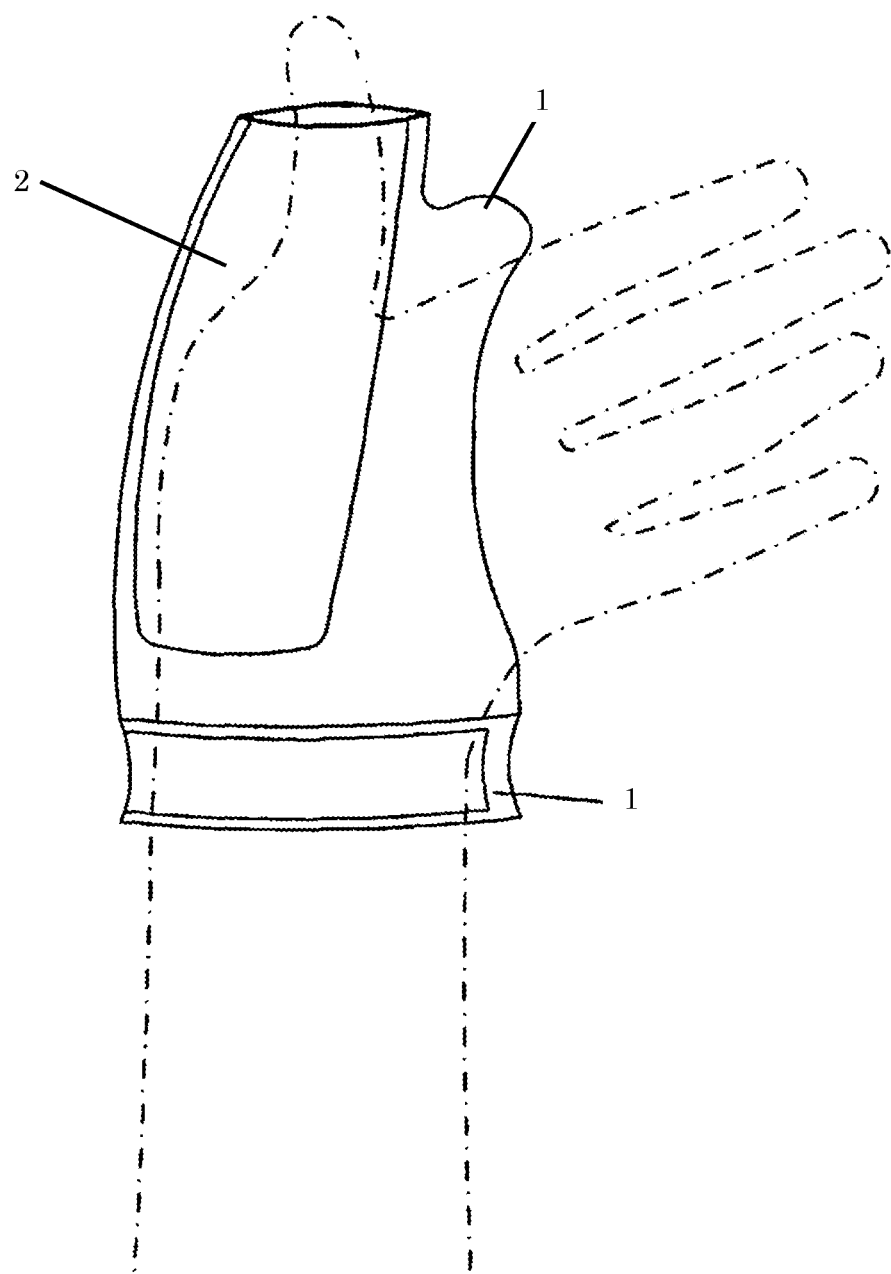
FIG. 1A shows a splint such as known from the state of the art, provided with a belt (1) for closing of the splint.

The nature of the thermoplastic polymer used in this invention is not critical to the invention. The thermoplastic polymer preferably has a melting point of up to 100.0° C., more preferably up to 70.0° C. However, thermoplastics having a high melting temperature, i.e., above 70.0° C. or above 100.0° C. which would normally not be suitable for direct moulding on the body part to be immobilized, may also be used. Preferably however, the thermoplastic polymer is selected from the group consisting of thermoplastic elastomers, thermoplastic polyurethane, thermoplastic poly-isoprene, thermoplastic polyesters, thermoplastic polyolefins, polyvinyl chloride, polystyrene, or a mixture of two or more of these polymers. Examples of suitable thermoplastic polyolefins include polyethylene, polypropylene, or ethylene-propylene co-polymers. Examples of suitable thermoplastic polyesters include polyethylene vinyl acetate, polyacrylate or polymethacrylate, polymeric fatty acid esters, in particular ε-polycaprolactone.

Materials which are especially preferred include thermoplastic polyurethane, isotactic polypropylene, a copolymer of ethylene with 1-butene, a copolymer of ethylene with 1-octene, ε-polycaprolactone, a blend of thermoplastic polyurethane and ε-polycaprolactone, as well as a mixture of two or more of the foregoing materials. The skilled person is able to select from the above group of materials, the most suitable material or mixture of materials.

ε-polycaprolactone which is for example marketed by Perstorp (UK) (under the trade name Capa) is particularly preferred because it has a low melting point, the material shows good moulding properties and has a sufficient elasticity in the molten state, for a sufficiently long period of time in order to allow for direct moulding on the body. This provides the possibility of applying changes to the shape of the immobilization element, even after the immobilization element has been produced by means of additive manufacturing. Such changes may be done to take into account changing dimensions of the body part to be immobilized in the course of time. If so desired, the ε-polycaprolactone can be used in a mixture with another thermoplastic, for example polyurethane.

In a preferred embodiment of the invention, the thermoplastic material is at least partially cross-linked.

Cross-linked thermoplastic materials suitable for use in this invention are described inter alia in EP2793767, for example, polycaprolactone, copolymers of polyethylene with at least one olefin having 3-10 C-atoms, or a mixture of two or more of these polymers, and a photo-initiator present to effectuate cross-linking by means of UV. Cross-linking usually leads to a polymer having an increased toughness and stiffness, a higher elasticity modulus and a higher stiffness of the thermoplastic in the molten or softened state. These material properties offer particular advantages, both in the course of the process of manufacturing of the immobilization element and thereafter.

By subjecting the polymeric material to crosslinking as soon as possible after having been molten, the viscosity of the polymeric material may be increased in an early stage, the risk to flowing of the molten material during additive manufacturing may be kept to a minimum, it may be ensured that the molten polymeric material is built up during additive manufacturing in accordance with a shape such as defined by the data set representative of the outer contours of the segment of the body part to be immobilized, and the use of a model or die that supports the three-dimensionally shaped immobilization element in the course of the additive manufacturing can be dispensed with. Cross-linked thermoplastic materials additionally have a certain memory. As a result hereof, after having been moulded into a first shape, they show a tendency to return to that first shape, after repeated heating. The skilled person is able to select the degree of crosslinking of the polymer in such a way that the material properties permit achieving an optimal processing in additive manufacturing.

Cross-linking of the thermoplastic material can be accomplished in various ways, these are known to the skilled person. Preferably however, use is made of a thermoplastic material which contains an amount of a photo initiator which upon exposure to UV light, generates radicals and initiates cross-linking or cross-linking of the thermoplast.

Compounds suitable for use as photo-initiator are known and include for example, benzoin, substituted benzoines for example benzoin ethyl ether, benzophenone, benzophenone derivatives, Michler's ketone, alpha-hydroxy ketone, benzyl dimethyl ketal, isopropyl thioxanthaan, dialkoxyacetophenonen such as diethoxyacetophenone, acetofenone, benzyl, and others and mixtures of the aforementioned compounds. The aforementioned compounds are particularly suitable for the cross-linking of the ε-polycaprolactone. The concentration of the photo-initiator can vary within wide limits and may for example be determined by empirically varying the degree of crosslinking and assessing which degree of crosslinking is capable of providing the optimal material properties for use in additive manufacturing. In general, the concentration of the photo-initiator will vary between 0.1-5.0 wt %, based on the weight of the polymer.

The thermoplastic material preferably also contains an amount of an accelerator, for enhancing the cross-linking. Preferably, as a cross-linking accelerator a polyfunctional cross-linking agent is used, which contains two or more reactive functional groups which after activation, are capable of forming a covalent bond with a functional group on the polymer. Accelerators with a low melting temperature (<100-120° C.), which show a good compatibility with polycaprolactone are preferred, in particular, tri-allyl cyanurate. Other examples of suitable accelerators are polyfunctional vinyl or allyl compounds such as tri-allyl isocyanurate, pentaerithritol tetramethacrylate, ethylene glycol, dimethacrylate, diallyl maleate, dipropargyl mono-allyl cyanurate and other derivatives and mixtures thereof. The concentration of the accelerator may vary within wide limits, but is preferably 0.01-2.0 wt. %, relative to the weight of the polymer.

The duration of exposure to UV light and the power of the UV source can vary within wide limits and are preferably chosen such that the desired degree of crosslinking may be achieved.

Nanomaterials.

In a preferred embodiment, the polymeric material contains nanoparticles as nucleating agent for enhancing the crystallization of the polymer material, in particular the crystallization of the thermoplastic polymer. Within the scope of this invention with nano-particles is meant particles of a material with a high length to diameter ratio, or a high surface area to thickness ratio. Nano particles are available in a wide range of materials known to the skilled person.

Suitable nanoparticles for use in this invention are for example described in WO2011/113473 and include minerals having a layered, lamellar structure, or a layered tubular structure. Examples hereof are layered mineral materials, for example layered silicates, mixed alumina-silica minerals such as clays, in particular phyllosilicates, e.g., montmorillonite, nontronite, beidelite, volkonskoite, hectorite, saponite, sauconite, magadiite, medmoniet, fluoro-hectorite, vermiculite, kaolin. Nano clay, for example, is available from Sid Chemie as "Nanofil" (montmorillonite), for example, "Nanofil 15" and "Nanofil 5", intercalated with distearoyldimethylammonium chloride; from Elementis Corp. (USA) under the name "EA 108" based on hectorite; from Southern Clay in particular Cloisite; Bentonite is available from Elementis Specialties. The above-described nano materials can be pre-treated with an organic compound in order to achieve intercalation of the layers and to improve the dispersibility in thermoplastic polymer.

The nano particles are preferably present as exfoliated particles. With exfoliation is meant that the layered structure of the mineral material is broken and that aggregates of platelets or lamellae are separated from one another and then dispersed in a plastic matrix. Thus, the thickness of the nano-particle is reduced to the order of magnitude of a few nanometers. In order to achieve exfoliation, various techniques known to the skilled person can be used. If so desired, the surface of the exfoliated particles can be modified to increase the compatibility with the thermoplastic polymer and to improve dispersibility.

Another suitable nano material comprises carbon nanotubes, which can be considered as one or more graphite layers rolled up into a cylinder. Carbon nanotubes are among others available at Nanocyl, Bayer MaterialScience, Arkema (Graphistrenght) and CNT Co. Within the scope of this invention both double-walled as multi-walled or single-walled carbon nanotubes can be used. This terminology is well known to the skilled person. Preferably, the carbon nanotubes are multi-walled since they may be produced in a more simple manner than single-walled nanotubes, which permits to reduce the cost price. The surface of the carbon nanotubes can be modified, for example with an organic compound in order to improve compatibility with the thermoplastic material and to enhance dispersibility.

Within the scope of this invention, the concentration of carbon nanotubes in the composite material can be varied within wide limits. Preferably, the concentration of carbon nanotubes is less than 2.0 wt. % relative to the weight of the composite material, preferably less than 1.5 wt. %, more preferably less than 1.0 wt. %. Increasing the concentration above the 2.0 wt. % can lead to a viscosity in the molten state, which may complicate the further processing of the material. Preferably, the concentration of carbon nanotubes is greater than 0.05 wt. %, preferably greater than 0.1 wt. %, more preferably greater than 0.25 wt. %. The dimensions of the carbon nanotubes may vary within wide limits. Preferably, the multi-walled carbon nanotubes have an inner diameter of 0.5-15 nm, preferably 3-7 nm, an outer diameter of 1-50 nm, preferably 5-25 nm and a length of maximum 100 nm, preferably maximum 75 nm, more preferably maximum 50 nm.

According to this invention the thermoplastic material may contain both nano clay particles and carbon nanotubes, if an enhanced synergistic effect is envisaged in which both the crystallization speed is increased and the mechanical properties of the composition are to be affected.

The nanoparticles may be contained in the polymeric material, it is however also possible to have the nano particles exclusively present in the thermoplastic polymer.

When account is taken of the additive manufacturing technique selected, the thermoplastic polymer or polymeric material may take the form of particles, a powder or a filament. Preferably, however a filament is used, more preferably a mono-filament as a mono-filament does not require the additional handling of twisting the fibers in order to ensure an optimal material mixing. In addition, the mono-filament preferably has a diameter between 0.5 and 5.0 mm, in particular between 1.0 and 4.0 mm, preferably between 1.0 and 3.0 mm. Mono filaments having such a diameter can be produced even if the thermoplastic polymer or polymeric material contains nanoparticles, and even with an incomplete exfoliation of the nanoparticles. This is especially important with FDM, since it is now possible that one material layer thickness suffices in thickness direction of the material for producing an immobilisation element or a mask in the desired thickness, without requiring a further processing of the material. This provides advantages to the production speed. The optimum fiber diameter can be selected by the skilled person, taking into account the intended application. A material thickness of 0.5 mm to 3.5 mm is preferred when manufacturing masks for use in radiation therapy and diagnostic techniques. The masks preferably have a sufficiently high degree of stability so that on the one hand the possibility to move the body within the mask is reduced to a minimum, and on the other hand the desired radiation transparency is ensured. Therefore, such masks are often made of a material having a thickness of 0.5-3.5 mm, preferably of 0.5 to 2.5 mm. Also, casts and splints preferably have a sufficiently high stability in order to restrict the possibility of the body part to move within the mask to the desired minimum or to allow a certain amount of motion, and to ensure that the segment of the body part is immobilized in the desired configuration. An orthesis or prosthesis, for example, are typically made of a material having a thickness of 0.5-4.5 mm.

The immobilization element may be manufactured exclusively of monofilaments of a polymeric material. It is however also possible to simultaneously with the continuous mono-filament of the polymer material, supply a continuous filament or fiber of a fibrous reinforcing material. As a result the polymeric material will be melted on the fibrous reinforcement material.

In case use is made of a multi-filament fiber, this fiber can also contain if so desired one or more fibers of a fibrous reinforcing material, in addition to one or more of the fibers of the desired thermoplastic polymer or polymeric material.

Suitable examples of fibrous reinforcement materials are mineral fibers, for example glass fibers, carbon fibers or polymeric fibers, or one or more fibers of a different thermoplastic material. In the method of the invention, the fibrous reinforcing material and the thermoplastic material are preferably deposited simultaneously in the shape that is being produced in order to ensure an optimal adhesion of both materials.

In an alternative embodiment, the polymeric material which contains a thermoplastic polymer takes the form of a powder, the particles of which have dimensions that are suitable for use in additive manufacturing, in particular, selective laser sintering, or any other additive manufacturing technique which makes use of particulate material.

Thermosetting Polymers.

According to this invention, the polymer material can also contain one or more thermosetting polymers in addition to at least one thermoplastic polymer, and the polymeric material may therefore be a blend of one or more thermoplastic polymers and one or more thermosetting materials.

The nature of the thermosetting material is not critical to the invention. Preferably, however, the thermosetting polymer is selected from the group of polyurethanes, silicones, phenol formaldehyde resins, urea formaldehyde resins, melamine, polyimides, cyanate esters, unsaturated polyester and epoxy resins.

Suitable materials for the manufacture of the immobilization element also include multi filament thermoplastic polymers, which prior to their use in additive manufacturing have been impregnated with a thermosetting resin, or materials which contain a fibrous reinforcing material which prior to being used in additive manufacturing has been impregnated with a thermosetting resin. It is however also possible to carry out the impregnation with the thermosetting resin in the outflow opening of the 3D printing apparatus.

Additive Manufacturing.

In the method of this invention a variety of additive manufacturing techniques can be used for the production of the immobilization element. Examples of suitable techniques include fused deposition modelling of one or more filaments, selective laser sintering of a powder and stereo lithography, but also other techniques known to the skilled person can be used. Common to all of these techniques is that the material from which the article is manufactured is applied or deposited in layers to permit building up of the final product in height direction, the polymer material is melted and the material is cooled down. The application and/or melting of the polymer material takes place according to a pattern controlled by the data set of a three-dimensional image of the object to be formed, that had been acquired in advance.

With fused deposition modelling, a continuous filament of the polymer material is supplied from a coil (3) to an extrusion opening (4), the polymer material is melted and extruded through a nozzle, and positioned on a support or platform (5) in a molten state. The thus deposited material has a certain thickness in the thickness and height direction of the shape. After a first layer (10) of the polymer material has crystallized or solidified, a subsequent layer (11, 12) is disposed on the previous layer. In this way layer by layer is built up in height direction. This is shown for example in FIG. 1D. The shape or the pattern according to which successive filaments are deposited, is controlled by the data set of the outer contours of at least a portion of the body part to be immobilized. In practice, the nozzle is moved over a platform on top of which the molten filament is deposited. The thin layer formed by the filament is cooled, hardens and binds directly to an underlying layer that had been deposited in advance. In the method of this invention, deposition of the filament is controlled in such a way that a hollow shape is provided the inner surface of which, or a portion thereof, has a shape or contour which corresponds to the outer contour of at least a portion of the body part to be immobilized.

If it is the intention to partially or fully crosslink the thermoplastic material present in the polymer material, cross-linking is carried out as soon as possible after deposition of the molten polymeric material and prior to the solidification or crystallization thereof. This may for example be achieved by providing, downstream of the outflow opening along which the polymeric material leaves the extrusion apparatus, a radiation source which effectuates the cross-linking. The radiation source is preferably positioned as close as possible to the outflow opening for the molten or softened polymeric material. In the case of selective laser sintering of a powder cross-linking may for example be accomplished by having the displacement of the radiation source which causes the selective melting of the powder to occur, followed by a radiation source which initiates cross-linking of the melted or softened polymer. Thereby, the time which elapses between the selective melting and cross-linking is preferably kept as short as possible.

In the method of this invention usually a hollow shape is manufactured, which is provided to at least partly cover or envelope the body part to be immobilized. In the method of this invention it may be selected to provide one single material thickness in thickness direction of the shape, for example a single filament as described above, and the shape may be build up by depositing a plurality of layers in height direction. In the context of this invention it is however also possible to produce the shape of two or more layers of the same polymer material or different polymer materials in the thickness direction, where the layers are joined to each other in the thickness direction of the mould.

It is further possible to compose the immobilization element of one single polymeric material or of different polymeric materials, that is, to compose the immobilization element in height direction of successive layers of different polymeric materials, in order to locally modify the properties of the immobilization element. It is also possible to compose the immobilization element in thickness direction of successive layers of the same or different polymer materials.

In case use is made of fused deposition modelling, according to this invention it is for example possible to make use of co-extrusion or extrusion of two or more filaments of the same material or of different materials, through two or more orifices, which in the thickness direction of the immobilization element are positioned adjacent to each other. Thus a layered material may be obtained which in thickness direction is composed of two or more adjacent material layers that are joined to each other. The adjacent layers are joined to each other during the deposition of the material, so that optimal adhesion of the layers can be guaranteed. Until now no techniques existed which permitted to achieve this. An appropriate choice of the material for the successive layers makes it possible to control the mechanical properties or the functional properties of the immobilization element taking into account the intended application. Thus, it is for example possible to apply simultaneously with the thermoplastic material, to the body-facing side of the shape a polymeric foam with which the comfort may be improved, a material which provides for a time-controlled release of a drug, a wound healing promoting material, an antibacterial material, a soft touch material, a moisture-absorbing material, a fibrous reinforcing material and the like. For example, it is also possible to apply simultaneously with the thermoplastic or a thermosetting material, a fibrous reinforcing material and to deposit the fibrous reinforcing material in accordance with the data set.

In selective laser sintering (SLS), use is made of granules or a powder of the polymeric material, the powder is applied layer-wise in height direction of the shape and a quantity of powder is selectively molten in thickness direction of the shape and sintered, in accordance with the data set comprising the three-dimensional image of an outer contour of the body portion to be immobilized. The powder may for example be applied using a scraping roller, and molten onto the previous layer. Because the molten polymer powder is surrounded by non-molten powder, no supporting structure is required to support the product while it is being produced. This method offers the advantage that it is suitable for use with a wide range of materials, ranging from nylon, polystyrene, steel and titanium to casting sand. The SLS technique permits to produce rather complex shapes using relatively simple means. In order to promote the smoothness of the surface an after-treatment may be recommended, such as for example irradiation and/or sliding grinding of the surface.

Stereolithography is particularly suitable for use with thermosetting polymers, wherein a layer of the thermosetting polymer is applied and cured with a laser. Thereafter, a new layer of a thermosetting material is applied. The 3-D object is formed by hardening several layers on top of each other, this is for instance described in U.S. Pat. No. 4,575,330.

The data set of the three-dimensional image of the outer contours of the body to be immobilized can be arranged in such a way that for example in the production of a mask or some other immobilization element, attaching profiles for connecting the mask to the patient table, are produced in one production step with the mask. The attachment means may be made from the same or from a different material.

The data set of the three-dimensional image can be provided such that for example in the production of a cast or splint, connecting means for joining edges are manufactured in one single manufacturing step with the cast or splint, so that closing of the shape and thus the desired immobilization or mobilization may be guaranteed, as shown in FIG. 1A. The data set of the three-dimensional image may further be arranged in such a way that in the course of the production, perforations are applied to the polymeric material. The invention offers the advantage that the position of the perforations, their individual size and shape, are adjustable. This way it is for example possible to provide no or a small number of perforations of relatively smaller dimensions at the positions where immobilization is desired, and a larger number of perforations with larger dimensions on the surrounding part of the immobilization element. This improves the comfort for the patient. It is also possible, with a layered material, to apply perforations which extend through the entire thickness of the material or through a part of the thickness only.

Imaging.

Techniques suitable for forming a three-dimensional image of the contours of the outer surface of the segment of the body part to be immobilized are known to the skilled person. For example, use can be made of one or more cameras, arranged at different positions in such a way that a desired portion of the body part can be imaged. The image data or image data thus obtained are stored. If necessary, these data can be edited, for example, to remove certain parts and to add additional parts. When imaging the head, for example the data corresponding to the neck and chin may be removed and the sides laterally of the face may be extended in such a way that the side of the immobilization element may be attached to the patient table. It is also possible to adapt the data in such a way that apertures or pores are provided in the material of the immobilization element. It is also possible to adapt the dimensions of the immobilization element or to apply positioning markers or indications related to a subsequent procedure.

In the course of the imaging process, the body part to be immobilized is preferably temporarily immobilized.

In general, the data set which is obtained from the imaging of the three-dimensional image of the contours of the outer surface of the segment of the body part to be immobilized will control the deposition of the polymeric material during additive manufacturing, for example in the course of fused deposition modelling, or melting of the polymer with sending selective laser sintering, but also in other additive manufacturing techniques shaping of the polymeric material will be controlled by the data set.

The method of this invention therefore preferably further comprises one or more of the following steps:

1. The generation of a three-dimensional image of the outer contours of the segment of the body part to be immobilized by non-invasive imaging and the organization of this image in a dataset. This image can be edited and converted into a surface model, an offset relative to the skin surface of the body part to be immobilized can be provided or not. The dataset may also be processed in such a way that it is suitable for controlling an additive manufacturing apparatus as described above. To this end, the data of the data set are for example sent to a data processing device which is provided with special image-processing software and stored therein. Through this software, the anatomical structure of interest (i.e. the head) is first separated from the 3-D) data set, stored, and then a particular data format, such as STL (data transmission format) is generated. The data file is then passed to an additive prototype device in a readable format.

2. The processing of the data set to permit the addition of one or more markers or to permit the removal of one or more parts from the material of the immobilization element.

If so desired, an offset value can be provided, so that the shape and dimensions of the immobilization element are arranged in such a way that the immobilization element can be kept at a certain distance from the body part to be immobilized. The presence of an offset value for example offers the possibility to increase the comfort for the patient, for example in the case of an immobilisation mask that is positioned on the head or the face, or to compensate for changes in shape and/or dimensions in the course of the period in which the mask is being used. The maintenance of an offset value also offers other possibilities such as a facilitated removal of the immobilization element by the patient and for example facilitate removal of a splint for a hand without having to destroy the splint.

The method of this invention makes it possible to provide very accurate immobilization elements, which fit tightly to the segment of the body part to be immobilized. Because the immobilization element is manufactured using a three-dimensional image of the segment to be immobilized, no factors are present that could cause unwanted deformation of the element.

This invention further relates to an individualized immobilization element for the non-invasive immobilize and/or mobilization of at least a segment of a body part of a patient in a predetermined configuration and/or at a predetermined position relative to a reference, obtained by the method as described above and described in the claims, wherein a contour of an inner surface of the immobilization element corresponds to at least a part of the outer contour of the segment of the body portion to be immobilised.

In a preferred embodiment, the immobilization element is made of one single material, and it is manufactured in its entirety using additive manufacturing. According to a particular embodiment, the immobilization element is made in a predetermined thickness, whereby the thickness can vary in function of the position on the immobilization element. This permits for example to provide a smaller layer thickness at the position of the part of the body which is provided to be contacted with high-energy radiation, and to provide a larger layer thickness at a position corresponding to the parts of the body which are to be shielded therefrom. In another preferred embodiment, the immobilization element comprises a first portion manufactured in a first material and a second portion manufactured in a second material. In a mask, the first part may for example be intended for covering of the portion of the segment that will be treated with radiation therapy, while the second part is intended to cover healthy tissue and to provide the part of the immobilization element which forms the connection to the table on which the patient is lying down.

Figure 1B:
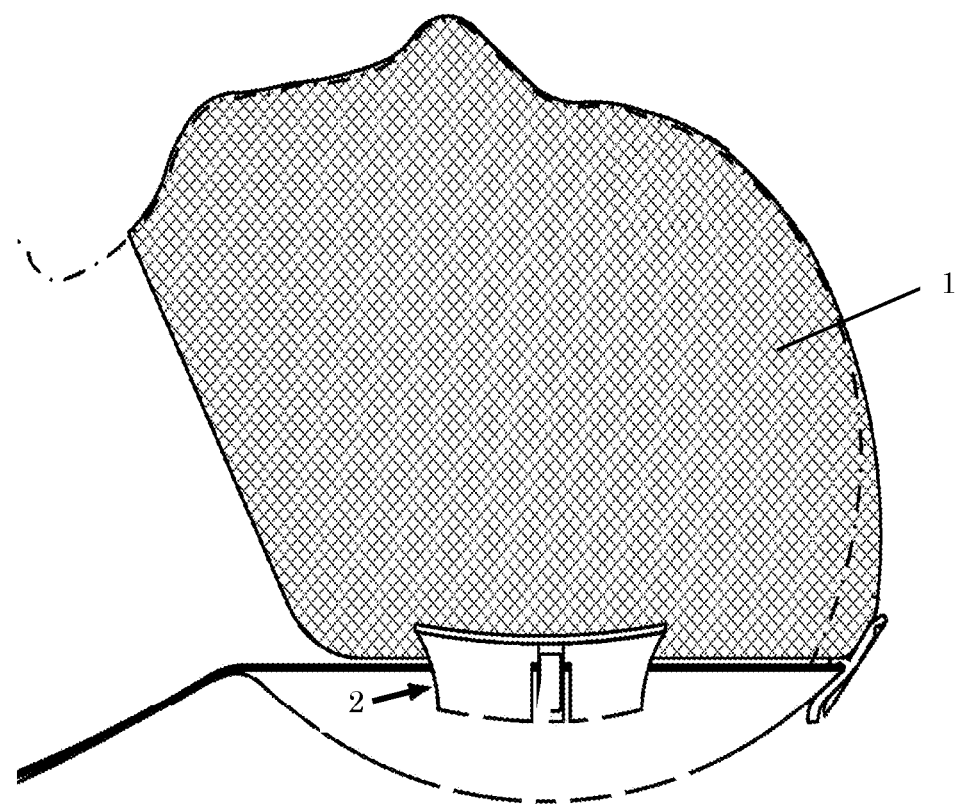
FIG. 1B shows an immobilization mask provided with connecting profiles (2) for attaching the mask to the table on which the patient rests.
Figure 1C:
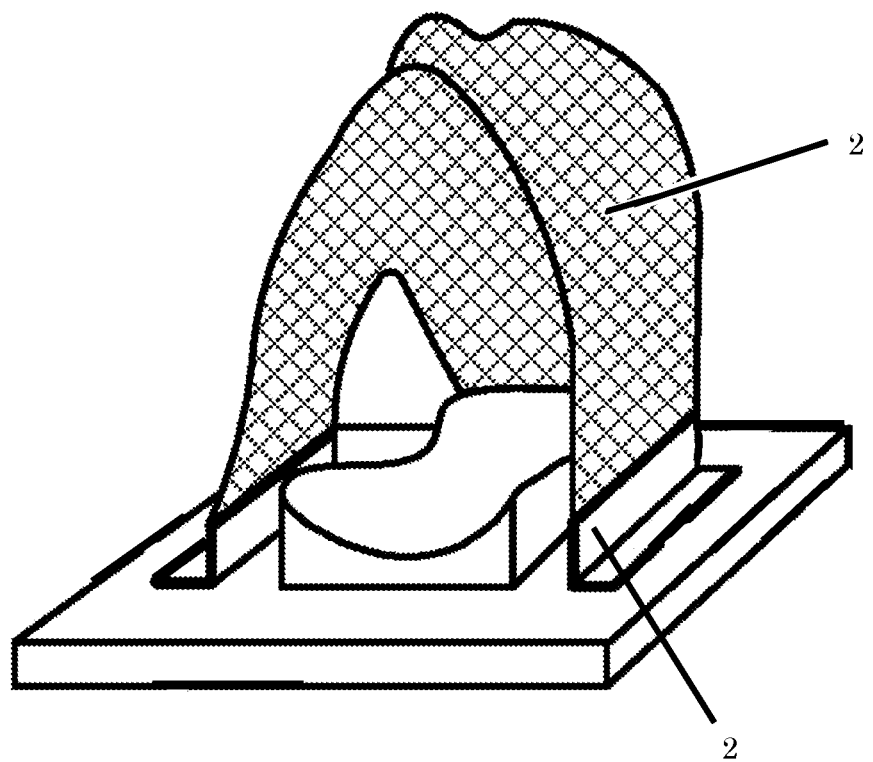
FIG. 1C shows an immobilization mask provided with connection profiles for attaching the mask to the table on which the patient rests.
Figure 1D:
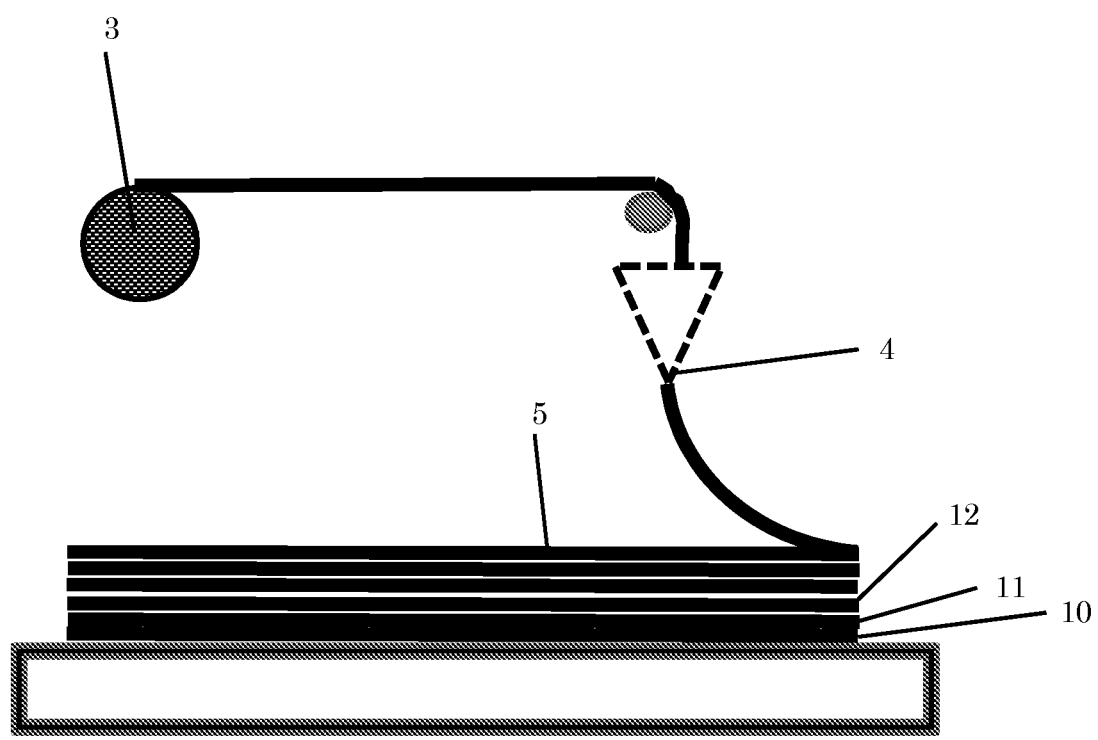
FIG. 1D shows the layerwise deposition of filaments of a thermoplastic material in fused deposition modelling.

This way it is also possible to produce the means for attaching a mask to the patient table (e.g., connecting profiles (2), shown in FIG. 1B) in a different material that does not melt or soften at the melting temperature of the thermoplastic material (1) from which the remaining part, the functional part, of the mask is manufactured.

This way it is for example also possible to apply a different material at the position of the eyes, for example, for example by using a material which may be removed in order to provide an opening at the level of the eyes. As removable material for example, use can be made of a thermoplastic polymer which has a melting temperature which is below the melting temperature or softening temperature of the thermoplastic polymer from which the remaining part of the immobilization element is made, for example, a melting temperature below 75° C., below 60° C., below 50° C., or below 45 or 40° C. An immobilization element may be produced as one part or it may be manufactured of two or more parts which are made of different materials and are connected to each other to form a single immobilization element. Editing of the data set permits to ensure that the desired material is deposited in the desired position.

In a further preferred embodiment, the immobilization element is manufactured from a laminated material, which in thickness direction of the material contains two or more adjacent layers of material. Successive layers in the thickness direction may be manufactured from the same or a different material. An immobilization element can be manufactured for example, of a first layer of a non-crosslinked polymer, in particular a non-crosslinked thermoplastic material and an adjacent second layer may be manufactured of the same or a different polymer, in particular, the same or a different cross-linked thermoplastic. An immobilization element can also be manufactured for example, of a first layer of a polymer, in particular a thermoplastic material which contains the nano-particles and an adjacent second layer of the same or a different polymer, in particular, the same or a different cross-linked thermoplastic. It is further possible to apply to the inner surface of the immobilization element a layer of a functional material, for example an anti-bacterial material, or a layer of a soft plastic or a plastic foam, for example, for improving the comfort. The use of such a functional layer is of particular importance in immobilization elements made by means of fused deposition modelling or selective laser sintering, because of the relatively large surface roughness, which may be formed.

An immobilization element made of a layered material can be manufactured by first manufacturing the element in the desired form in the first material by means of additive manufacturing, and in a separate production step, successively one or more subsequent layers of material may be applied. Preferably, however, all the layers of material are deposited simultaneously, because this shortens the production time and ensures optimum adhesion between successive layers.

In another preferred embodiment, a layer of a second material can be applied to the inner surface of the immobilization element. This is particularly applicable for Fused Deposition Modelling of filaments, in which the joined filaments give rise to a certain degree of surface roughness, and it may be desirable for the inner surface of the immobilization element which may contact the skin of the patient, to provide a more comfortable material touch, for example a foamed polymeric foam.

In another preferred embodiment, fastening means for connecting the edges of the immobilization element are made integral with the immobilization element.

The immobilization element of this invention further contains the components as described above, and is made from the materials as described above.

The invention claimed is:

1. A method for manufacturing an individualized immobilization element for the non-invasive immobilization and/or mobilization of at least a segment of a body part of a patient at a predetermined position relative to a reference and/or in a predetermined configuration, the method comprising:
providing a data set that comprises a three-dimensional image of an outer contour of at least a portion of the segment of the body part to be immobilized and/or mobilized; and
manufacturing of at least a part of the immobilization element by rapid manufacturing of a shape based on the data set, using a polymeric material containing a thermoplastic polymer having a melting point less than or equal to 100° C.,
wherein the polymeric material contains a nucleating agent capable of enhancing crystallization of the thermoplastic polymer,
wherein at least a portion of an inner surface of the shape has an inner contour which is complementary to the outer contour of the segment of the body part to be immobilized and/or mobilized, and
wherein the immobilization element is manufactured by extrusion of a filament or co-extrusion of two or more filaments of the same or a different polymeric material and deposition of a plurality of successive filaments according to a pattern controlled by the data set.

2. The method according to claim 1, wherein the polymeric material comprises nanoparticles as a nucleating agent for enhancing the crystallization of the thermoplastic polymer.

3. The method according to claim 2, wherein the thermoplastic polymer contains between 0.01 and 10 wt. % of carbon nano-tubes, relative to a weight of the thermoplastic polymer.

4. The method according to claim 3, wherein the carbon nano-tubes are carbon nanotubes having a multi-layer wall.

5. The method according to claim 2, wherein the thermoplastic polymer contains between 1.0 and 15.0 wt. % of a organically modified clay, relative to a weight of the thermoplastic polymer.

6. The method according to claim 1, wherein the thermoplastic polymer is selected from the group consisting of thermoplastic elastomers, thermoplastic polyurethane, thermoplastic polyisoprene, thermoplastic polyesters, thermoplastic polyolefins, polyvinyl chloride, polystyrene, and a combination of two or more of these polymers.

7. The method according to claim 6, wherein the thermoplastic polymer comprises ε-polycaprolactone.

8. The method according to claim 1, wherein the at least one filament is a monofilament of the polymeric material.

9. The method according to claim 8, wherein the at least one filament has a diameter between 0.5 and 5.0 mm.

10. The method according to claim 1, wherein the polymeric material comprises at least one thermosetting resin.

11. The method according to claim 1, wherein a layer of the polymeric material is deposited in a molten state, according to a pattern controlled by said data set, and in the molten state is at least partially cross-linked, after which the polymeric material is cooled.

12. The method according to claim 1, wherein the deposition is by fused deposition modeling.

13. The method according to claim 1, wherein the at least one filament is at least partially cross-linked after extrusion and deposition.

14. The method according to claim 1, wherein two or more polymeric materials are co-extruded in a thickness-direction of the immobilization element such that the immobilization element contains two or more layers of polymeric material in the thickness direction of the immobilization element, and
wherein a first layer of polymeric material comprises a first thermoplastic polymer and a second layer of polymeric material comprises a second thermoplastic polymer.

15. The method according to claim 1, wherein simultaneously with the extruding the at least one filament, a filament is extruded of a fibrous reinforcement material.

16. The method according to claim 1, wherein the immobilization element comprises a first part manufactured out of a first polymeric material comprising a first thermoplastic polymer and a second part is manufactured out of a second material different from the first polymeric material.

17. An individualized immobilization element for the non-invasive immobilization and/or mobilization of at least a segment of a body part of a patient in a predetermined configuration and/or at a predetermined position relative to a reference, obtained by the method of claim 1, comprising:
a first portion manufactured of a first material and configured to cover the segment of the body part; and
a second portion manufactured of a second material and configured to cover healthy tissue of the patient,
wherein a contour of an inner surface of the immobilization element corresponds to at least a part of the outer contour of the segment of the body part to be immobilized.

18. The individualized immobilization element according to claim 17, at least partly manufactured from a laminated material.

19. The individualized immobilization element according to claim 18, wherein a layer of the second material is applied to the inner surface of the immobilization element.

20. The individualized immobilization element according to claim 17, wherein one or more fasteners for connecting one or more edges of the immobilization element with a support for the patient, are manufactured in one part with the immobilization element.

21. The individualized immobilization element according to claim 17, at least in part made of ε-polycaprolactone.

* * * * *